(12) United States Patent
Swartjes et al.

(10) Patent No.: US 12,115,356 B2
(45) Date of Patent: Oct. 15, 2024

(54) DEVICE AND METHOD FOR THE DELIVERY OF A THROMBIN ACTIVATED FIBRIN SEALANT

(71) Applicant: GAMBRO LUNDIA AB, Lund (SE)

(72) Inventors: Jan Swartjes, Tubingen (DE); Stefanie Votteler, Reutlingen (DE); Markus Storr, Filderstadt (DE); Bernd Krause, Rangendingen (DE)

(73) Assignee: GAMBRO LUNDIA AB, Lund (SE)

( * ) Notice: Subject to any disclaimer, the term of this patent is extended or adjusted under 35 U.S.C. 154(b) by 620 days.

(21) Appl. No.: 17/433,624

(22) PCT Filed: Mar. 6, 2020

(86) PCT No.: PCT/EP2020/055975
§ 371 (c)(1),
(2) Date: Aug. 25, 2021

(87) PCT Pub. No.: WO2020/178419
PCT Pub. Date: Sep. 10, 2020

(65) Prior Publication Data
US 2022/0143320 A1 May 12, 2022

(30) Foreign Application Priority Data
Mar. 6, 2019 (EP) .................................... 19161051

(51) Int. Cl.
*A61M 5/31* (2006.01)
*A61L 24/00* (2006.01)
(Continued)

(52) U.S. Cl.
CPC ....... *A61M 5/3145* (2013.01); *A61L 24/0036* (2013.01); *A61L 24/043* (2013.01); *A61M 5/19* (2013.01); *A61M 5/31505* (2013.01)

(58) Field of Classification Search
CPC .. A61M 5/3145; A61M 5/19; A61M 5/31505; A61L 24/0036; A61L 24/043;
(Continued)

(56) References Cited

U.S. PATENT DOCUMENTS

| | | | | |
|---|---|---|---|---|
| 5,432,062 A | * | 7/1995 | Turecek | C12N 11/14 435/68.1 |
| 5,607,694 A | * | 3/1997 | Marx | A61P 7/04 424/424 |

(Continued)

FOREIGN PATENT DOCUMENTS

| | | | | |
|---|---|---|---|---|
| CN | 103037783 A | * | 4/2013 | A61L 24/0031 |
| EP | 0839498 | | 5/1998 | |

(Continued)

OTHER PUBLICATIONS

PCT Search Report and Written Opinion prepared for PCT/EP2020/055975, completed Apr. 27, 2020.

(Continued)

*Primary Examiner* — Bob Zadeh
(74) *Attorney, Agent, or Firm* — Barnes & Thornburg LLP

(57) ABSTRACT

The invention relates to a dispenser of a sealant for hemostasis comprising a container configured to receive a fibrinogen solution and an activation compartment being situated downstream of the container and comprising a functionalized support to which a coagulation factor, preferably thrombin, is immobilized, such that upon dispensing the fibrinogen solution it passes through the activation compartment, thereby generating and dispensing polymerizing fibrin as a sealant. The invention further relates to a support, exchangeable tip and a kit for the dispenser as well as to methods and uses of the dispenser or components thereof for dispensing a sealant to a desired site.

23 Claims, 3 Drawing Sheets

Figure 1:
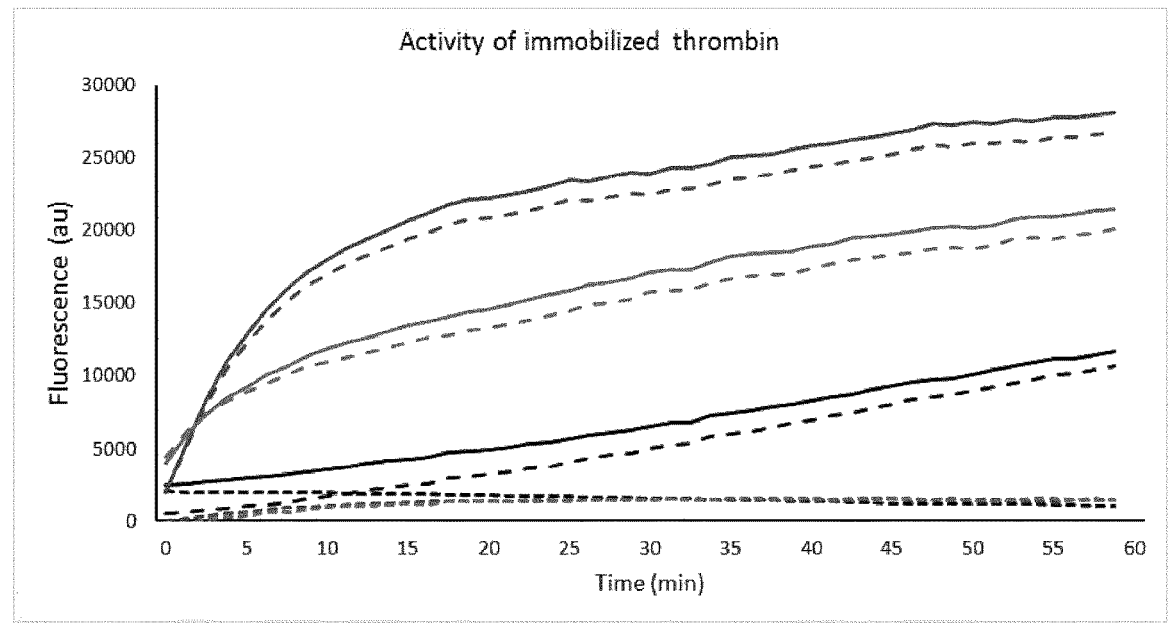

(51) Int. Cl.
*A61L 24/04* (2006.01)
*A61M 5/19* (2006.01)
*A61M 5/315* (2006.01)

(58) Field of Classification Search
CPC .......... A61K 38/363; C12Y 304/21005; A61B 2017/00495; A61B 2017/00526; A61B 17/00491
See application file for complete search history.

(56) References Cited

U.S. PATENT DOCUMENTS

| | | | | |
|---|---|---|---|---|
| 5,844,087 | A * | 12/1998 | Zimmerman | A61B 17/00491 604/196 |
| 6,121,422 | A * | 9/2000 | Zimmerman | A61L 24/106 604/196 |
| 6,168,788 | B1 * | 1/2001 | Wortham | A61L 24/108 424/443 |
| 8,821,861 | B2 * | 9/2014 | Smith | A61L 24/001 424/94.1 |
| 8,962,033 | B2 * | 2/2015 | Ilan | A61P 17/00 424/499 |
| 2008/0206298 | A1 | 8/2008 | Burkinshaw et al. | |
| 2013/0202656 | A1 | 8/2013 | Ericson | |
| 2014/0222067 | A1 * | 8/2014 | Ericson | A61B 17/0057 606/213 |
| 2015/0272562 | A1 * | 10/2015 | DeAnglis | A61K 38/36 604/311 |
| 2019/0343981 | A1 * | 11/2019 | Hammersh?j | A61L 15/64 |

FOREIGN PATENT DOCUMENTS

| | | | | |
|---|---|---|---|---|
| WO | WO-2012006147 | A1 * | 1/2012 | ......... A61B 17/0057 |
| WO | WO-2013131520 | A2 * | 9/2013 | ............. A61B 17/00 |

OTHER PUBLICATIONS

XP055491066; "BioProcess ProductGuide" 2012/2013; Apr. 7, 2012; BioProcess Product Guide; GE Healthcare Life Sciences, SE.

* cited by examiner

DEVICE AND METHOD FOR THE DELIVERY OF A THROMBIN ACTIVATED FIBRIN SEALANT

CROSS-REFERENCE TO RELATED APPLICATIONS

This application is a national stage entry under 35 U.S.C. § 371(b) of PCT International Application No. PCT/EP2020/055975, filed Mar. 6, 2020, which claims the benefit of European Patent Application Serial No. 19161051.8, filed on Mar. 6, 2019, the entire disclosures of both of which are incorporated herein by reference.

The invention relates to a dispenser of a sealant for hemostasis comprising a container configured to receive a fibrinogen solution and an activation compartment being situated downstream of the container and comprising a functionalized support to which a coagulation factor, preferably thrombin, is immobilized, such that upon dispensing the fibrinogen solution it passes through the activation compartment, thereby generating and dispensing polymerizing fibrin as a sealant. The invention further relates to a support, exchangeable tip and a kit for the dispenser as well as to methods and uses of the dispenser or components thereof for dispensing a sealant to a desired site.

BACKGROUND OF THE INVENTION

A fibrin sealant is typically a surgical hemostatic agent derived from plasma coagulation proteins. Fibrin sealants are widely used to control bleeding in a variety of surgical settings, and their use has increased due to the advent of minimally invasive surgical procedures which necessitate meticulous hemostasis for adequate visualization of the surgical field. Fibrin sealants can be used for hemostasis, wound closure, and tissue sealing and have been advocated as the agents that are closest to approaching the ideal operative sealant. In contrast to synthetic adhesives, fibrin sealants have the advantage of being biocompatible and biodegradable, and they are not associated with inflammation, foreign body reactions, tissue necrosis, or extensive fibrosis. Reabsorption of the fibrin clot is achieved during normal wound healing within days to weeks of application, depending on the type of surgery, the proteolytic activity of the treated site, and the amount of sealant used. Experience in animals and humans suggests that another advantage of using fibrin glue rather than synthetic plastics (e.g., cyanoacrylate) or sutures is that fibrin glue promotes local coagulation, thereby preventing bleeding even in hemophiliacs. Fibrin glue also appears to support regrowth of new tissue and the extracellular matrix.

Fibrin sealants are typically derived from plasma proteins and contain two primary components: fibrinogen and a coagulation factor such as thrombin. These two components are stored separately and are mixed during application. Upon mixing, thrombin induced activation of fibrinogen results in the formation of fibrin monomers. Polymerization of fibrin monomers results in the formation of a semi-rigid fibrin clot that is capable of interacting covalently and non-covalently with tissue structures. The clot may be further stabilized by cross-linking of the fibrin alpha and gamma chains in a reaction catalyzed by activated factor XIII. This cross-linking stimulates adherence of fibroblasts and promotes their normal growth into the clot. By mimicking the latter stages of the physiologic coagulation system, these processes allow fibrin sealants to arrest blood loss and assist the wound healing process.

The rate of coagulation and mechanical properties of the clot are dependent on the concentration of fibrinogen as well as thrombin. Traditional fibrin glue preparations are described in International Application No. WO93/05067 to Baxter International, Inc.; WO92/13495 to Fibratek, Inc.; and WO91/09641 to Cryolife, Inc.

Most commercially available fibrin sealants contain purified, virally inactivated human fibrinogen and either human or bovine thrombin, optionally with different quantities of factor XIII and antifibrinolytic agents (such as bovine aprotinin).

For instance, products as Tisseel, Artiss, Prevleak, Evicel and Beriplast P are typically marketed as a two-component kit: a first component contains human fibrinogen/factor XIII concentrate, which may be reconstituted with antifibrinolytic solution (aprotinin); and a second component is thrombin as a coagulation factor reconstituted with e.g. with $CaCl_2$.

The two-component fibrin sealants are usually applied through a double-barreled syringe system, which is designed for an application of equal volumes of the fibrinogen and thrombin through a blunt-ended needle or spray tip. Tisseel and Artiss employ a pre-filled two-component double syringe system, and an applicator which mixes the two-components upon application. Evicel equally makes use of a double syringe system, but releases the fibrin sealant as a spray.

The known two-component fibrin sealants perform very well in hemostasis, that is the fibrin sealants adhere well to the tissue and reliably stop the bleeding acting as an effective bioadhesive, that is readily absorbed during subsequent wound healing.

The double syringe systems impose however practical challenges for medical practitioners and surgeons. In particular, the limited stability of the components when thawed requires a very quick handling of the system, which may result in suboptimal deposition of the fibrin sealant. Furthermore, current delivery systems transfer significant amounts of thrombin contents at the wound site, which may interfere with the sealing dynamics, wound healing or reabsorption of the fibrin clot.

In the prior art alternative approaches for simplifying delivery systems for fibrin sealant have been disclosed, for example in U.S. Pat. No. 6,121,422. However, the system described therein requires further development, as the dispenser may interfere with the activity of the components and thus compromises the sealant function.

SUMMARY OF THE INVENTION

In light of the difficulties in the prior art, the technical problem underlying the present invention is the provision of improved or alternative means for the deposition of a fibrin sealant, which in particular allows for a simpler, more precise and less error prone handling and an increased control over components reaching the wound site.

The solution to the technical problem of the invention is provided in the independent claims. Preferred embodiments of the invention are provided in the dependent claims.

The invention therefore relates to a dispenser of a sealant for hemostasis, comprising:
 a container configured to receive a fibrinogen solution, and
 an activation compartment,
the activation compartment being situated downstream of the container and comprising a functionalized support to which a coagulation factor is electrostatically immobilized, wherein the functionalized support is a functionalized resin comprising particles with a mean size of 150 to 300 μm.

The dispenser of the present invention allows for a particularly easy handling and precise deposition of a two-component sealant for hemostasis. The dispenser of the present invention also shows excellent activity of the coagulation factor, such as thrombin, thereby leading to more effective generation of fibrin monomers, subsequent polymerization and therefore effective sealant formation.

The container is configured for receiving a fibrinogen solution and may in preferred embodiments be prefilled with a fibrinogen solution or freeze-dried fibrinogen. Downstream of the container, the dispenser comprises an activation compartment in which a coagulation factor such as thrombin is immobilized. Prior to dispensing, the design ensures a separation of the two components, the fibrinogen solution and the immobilized coagulation factor, preferably a fibrinogen-cleavage protease such as thrombin.

In this state the dispenser may thus be stored, freely moved or transported without the risk of a mixing of the components prior to dispensing. In preferred embodiments the dispenser may comprise between the activation compartment and the container additional separation means such as a membrane to reduce passive diffusion of the fibrinogen into the activation compartment.

The position of the activation compartment downstream of the container ensures that upon dispensing, the fibrinogen solution will pass said activation compartment. To this end the dispenser may comprise a piston equipped with a plug for extruding a fibrinogen solution from the container through the activation compartment. The dispenser may in preferred embodiments be provided in form of a single-barrel syringe with a downstream activation compartment that can easily be operated manually by pushing a plunger. The user of the device therefore is not presented with any difficulty in plunging, or dispensing the sealant, as essentially only a single chamber must be expunged, pushing the fibrinogen through a downstream compartment. Difficulties arise frequently in the systems of the prior art with two adjacent chambers, which require equal pressure to be applied to both chambers upon expulsion.

While passing through the activation compartment the fibrinogen solution will be activated by the immobilized coagulation factor for hemostasis and yield polymerizing fibrin as a sealant The reduction of the number of components of the dispenser and a reduction in complexity of the device compared to prior art solutions improves the ease of use considerably. Additionally, the immobilization of the coagulation factor, such as thrombin, increases the stability of the component. Another valuable advantage is that comparably less of the coagulation factor is deposited in the wound area compared to a typical doubled-barrel syringe system. The activation compartment of the present invention represents a significant improvement over the prior art, showing multiple benefits that work in unison to provide a more effective sealant production. The activation compartment as described herein enables excellent activity of the immobilized coagulation factor whilst maintaining more coagulation factor in the device, thereby depositing less in the wound site. This combination of advantages leads to a superior device. Thereby a better control over the sealing dynamics may be reached and interference with the endogenous wound healing process or reabsorption is minimized.

Optimal results for a deposition of fibrin sealant are achieved, when the coagulation factor, preferably thrombin, is electrostatically immobilized on a functionalized resin comprising particles with a mean size of 150 to 300 μm.

These conditions appear to result in a synergistic effect that ensures a high stability and activity of the coagulation factor to induce fibrinogen cleavage, while preventing undesired release of the coagulation factor into the site of deposition.

As shown in the data below, an electrostatically immobilized thrombin exhibits a significant increased cleavage activity for fibrinogen compared to covalent attachments. Without intending to be bound by theory, it is conceivable that the covalent immobilization impedes the conformational variation necessary for the cleavage function, while a 'weaker' electrostatic immobilization does not. Nevertheless, surprisingly, an electrostatic immobilization does not result in a significant increase of the amounts of coagulation factor leaching from the activation compartment into the deposition site, when immobilized on particles with a mean size of in between 150 and 300 µm.

Moreover, the preferred particle sizes of the functionalized resin lead to elevated initial immobilization yields and promote a fibrinogen cleavage activity of a coagulation factor such as thrombin.

The size distribution of resin particles further positively influences the flow velocity, pressure distribution as well as the dwell time of the fibrinogen solution within the activation compartment in a typical mode of operation.

A typical mode of operation may, in some embodiments, relate to the dispenser as a syringe comprising a piston or plunger that can be manually operated for dispensing the sealant. Typically applied forces using a thumb for operating a syringe range in the order of 5-50 Newtons (K. Asundi et al. The Journal of the Human Factors and Ergonomics Society: 67-75, February 2005). For such forces a range of mean particles sizes in between 150 µm and 300 µm results in a flow velocity and dwell time of a fibrinogen solution in the activation compartment that ensures efficient conversion of fibrinogen into monomeric polymerizing fibrins. At the same time excessive fluid shear forces and pressure built-up are prevented that otherwise may promote dissociation of the immobilized coagulation factor from the resin particles.

Advantageously, the dispenser exhibits therefore reproducible deposition of a fibrin sealant with desired properties for hemostasis, irrespective of the exact mode of operation. By design variations in the quality of the fibrin sealant due to slightly different manual operations are minimized. Furthermore, no special set of skills are necessary for operating the dispenser.

Instead, the invention provides a dispenser that is easy to use and by design ensures reproducible, precise deposition of a fibrin sealant to a wound area or any other desired site that may require hemostasis.

A beneficial mode of operation may be further aided by a preferred design and dimension of the activation compartment. Optimal results are achieved with an activation compartment having a length of 1 mm-20 mm, preferably 4 mm-15 mm and a cross-sectional area of in between 10 $mm^2$-400 $mm^2$, preferably 25 $mm^2$-100 $mm^2$. In some embodiments, the activation compartment is cylindrical. Herein, the length of the activation compartment refers to the dimension along the direction of dispensing the fibrinogen solution, while the cross-sectional area refers to the area orthogonal to the direction of dispensing the fibrinogen solution. In some embodiments, intermediate ranges of the above-mentioned dimensions may be preferred.

In some embodiments the activation compartment may have a preferred length of 2 mm-4 mm, 4 mm-6 mm, 6 mm-8 mm, 8 mm-10 mm, 10 mm-12 mm, 12 mm-14 mm, 14 mm-16 mm, 16 mm-18 mm or any combination of said intermediate ranges, without limitation, such as e.g. 4 mm-8 mm, or 6-14 mm.

In some embodiments the cross-sectional area of the activation compartment may preferably be in between 10 mm$^2$-25 mm$^2$, 25 mm$^2$-50 mm$^2$, 50 mm$^2$-75 mm$^2$, 75 mm$^2$-100 mm$^2$, 100 mm$^2$-150 mm$^2$, 150 mm$^2$-200 mm$^2$, 200 mm$^2$-250 mm$^2$, 250 mm$^2$-300 mm$^2$, 300 mm$^2$-350 mm$^2$ or 350-400 mm$^2$ or any combination of said intermediate ranges, without limitation, such as 50 mm$^2$-200 mm$^2$ or 100 mm$^2$-300 mm$^2$.

In one embodiment the coagulation factor is a fibrinogen-cleaving protease, preferably thrombin.

In one embodiment the functionalized resin is an amino-functionalized resin, preferably an amino methacrylate resin.

An amino-functionalized resin refers to a resin that comprises amino or amine groups as functional groups, wherein the groups may be primary, secondary, tertiary or quaternary amino groups. Most preferably an amino-functionalized resin comprises —NH$_2$ as a functional group.

Amino-functionalized resins allow for an electrostatic immobilization of proteins such as the coagulation factor by ionic interaction of the ionizable surface amino acids with the charged amino-groups on the resin particles. As the data show below, an amino-functionalized resin exhibits a particularly high immobilization yield combined with elevated protein activity, as is the case for thrombin, as demonstrated by its cleavage capacity of fibrinogen.

In one embodiment the functionalized resin is a methacrylate resin.

In a preferred embodiment the functionalized resin is an amino methacrylate resin. Using both methacrylate polymers for the resin and providing amino groups for an electrostatic immobilization yields particular good results in regards to protein activity and immobilization yield.

In one embodiment the functionalized resin comprises a spacer moiety to which a functionalized group is attached.

In one embodiment the spacer moiety comprises or consists of an organic moiety comprising $C_2$-$C_{20}$, preferably $C_3$-$C_{10}$, preferably a branched or unbranched alkyl, alkenyl, alkynyl, aryl, aminoalkyl, aminoalkenyl, aminoalkynyl, amide and/or aralkyl group, or combination thereof.

The spacer moiety allows the functional groups such as the amino groups to move more freely about the surface of the particles of the resin, thereby promoting conformational and transitional freedom of the immobilized coagulation factor. Furthermore the spacer moiety minimizes possible steric interaction of the immobilized coagulation factor with the particle surface, which may deprive protein activity.

Particularly good results are achieved for the above-mentioned spacer moieties, wherein hexamethylene or a similar C6-long spacer moiety is used.

In one embodiment at least 2000 units (U), preferably at least 5000 U, more preferably at least 10000 U of the coagulation factor are immobilized per gram (g) of the support. Said concentration of the coagulation factor, preferably thrombin, provides optimal conversion rates for a fibrinogen solution in order to yield highly adhesive and polymerizing fibrin sealants.

In one embodiment the resin particles are porous particles with a mean pore diameter of in between 60 nm and 120 nm, preferably 60 nm to 100 nm, more preferably 70 nm to 90 nm. The pore sizes augment the reactive surface and represent an optimal set of conditions for electrostatic immobilization, in particular in combination with mean particle sizes of in between 150 µm and 300 µm.

In one embodiment the mean particle size is more than 150 µm, 160 µm, 170 µm, 180 µm, 190 µm or more and less than 300 µm, 290 µm, 280 µm, 270 µm, 260 µm, 250 µm, 240 µm, 230 µm, 220 µm, 210 µm or less. Preferably the mean particle size is in between 180 µm and 220 µm most preferably approximately 200 µm.

Resins are typically produced by suspension, namely a polymerization process which, when followed by functionalization, results in a spread of the particle sizes about the mean.

The preferred embodiment may thus relate to resins with a mean particle sizes for instance approximately 200 µm and a range of particle sizes that are present in the resin, for instance 150 µm to 300 µm. The spread of the size distribution can be quantified by a standard deviation.

In one embodiment the size distribution of the particles have a standard deviation of 40 µm or less, preferably 30 µm or less.

In one embodiment the size distribution of the particles have a standard deviation of 5 µm, 10 or more.

A minor variation of the particle size about the mean as defined by the above-mentioned standard deviations allows for improved packing of the particles in the activation compartment and lengthen dwell time of the fibrinogen solution. However, a too large of a spread may lead to reduced immobilization yield and activity, since the proportion of particles with a less favorable sizes augments the properties of the activation compartment.

In one embodiment the dispenser additionally comprises a piston equipped with a plug, said plug being configured to be received in the container and for extruding a fibrinogen solution from the container and through the activation compartment. The plug is preferably dimensioned such that the outer cross-sectional-area of the plug covers the inner cross-sectional area of the container leading to a (material tight, or waterproof) separation of a first volume in the container downstream of a plug and a second volume of the container upstream of the plug. By moving the piston to which the plug is attached the fibrinogen solution situated in the first volume is transferred into the downstream activation compartment. The piston and plug can be made of any suitable material, including any synthetic material, flexing plastic, non-flexing plastic, glass and/or rubber as long as the plunging function of the piston and plug is maintained. In preferred embodiments the piston and plug are inert materials without any effect on the biological components of the system.

In a further embodiment the dispenser additionally comprises a filter situated downstream of the activation compartment, wherein said filter is configured to prevent release of the functionalized support.

The filter is preferably a physical filter that allows fluids including proteins such as fibrin to pass, but blocks solids such as the particles of the resin. The filter pore size may be adapted to the functionalized support and is preferably chosen such that the smallest particles of the resin cannot pass. For instance for a resin with a mean particle size of 200 µm and a spread of particles from 150 µm to 300 µm, the filter pore size will be preferably substantially less than 150 µm in order to secure that any part of the resin is prevented from reaching the deposition site. Preferred pore sizes for the filter are in the range of 0.2 µm to 10 µm, preferably 0.5 µm to 5 µm. Membranes and suitable filters are known to a person skilled in the art.

In one embodiment the dispenser comprises a main body comprising the container and an exchangeable tip, wherein the activation compartment is comprised in the exchangeable tip or the main body. The main body refers to the component of the dispenser that comprises the container and possible further elements such as the activation compartment.

As used herein the term "exchangeable" in the context of the tip means that the tip can be reversibly attached to the main body. To this end the exchangeable tip and the main body may comprise means for a releasable attachment. For instance, the main body receiving end of the exchangeable tip may comprise a male screw thread, while the main body tip receiving end may comprise a counter female screw thread. However, also other means for releasable attachment may be envisioned including bayonet mounts, snap fasteners, clamps, clips or the like.

Employing an exchangeable tip allows for a flexible and resource efficient use of the dispenser. For instance, the same main body may be use repeatable times for dispensing a fibrin sealant, wherein between each use the main body is sterilized and refilled with a fibrinogen solution.

For some embodiments it may be also preferred to provide exchangeable tips with different extrusion ends for deposition of the fibrin sealant. The exchangeable tips may for instance differ in the size of a needle diameter or length to provide optimal guidance depending on the application.

In a first alternative of the embodiment the activation compartment is situated within the main body, i.e. downstream of the container, but preferably located within the same structure forming the main body. In this case the exchangeable tip is releasable attachable to the activation compartment or the part of the main body just downstream of the activation compartment. In case that the dispenser comprises a filter, it is preferred that the filter is part of the main body.

In a second alternative of the embodiment the activation compartment is situated within the exchangeable tip. In such cases, it is preferred that a filter is positioned within the exchangeable tip on the receiving end for the main body. Advantageously, in such an embodiment a main body of a common syringe with a container suitable to receive a fibrinogen solution may be used for a connection to the exchangeable tip that contains the immobilized coagulation factor as described herein. The embodiment allows thus for a particular efficient use of resources.

Furthermore, by separating the container for receiving the fibrinogen solution and the activation compartment comprising the immobilized coagulation factors storage flexibility is gained. For instance, the exchangeable tip with the immobilized coagulation factor may be stored at 4° C., while the container is provided with a prefilled fibrinogen solution and stored at −20° C. or vice versa. Optimal storage conditions can be defined for each of the components.

In one embodiment the container is filled with a solution comprising fibrinogen, preferably human fibrinogen.

Preferred concentrations for the content of fibrinogen in the solution range in between 5 and 30 wt % (percent per weight). In some embodiments, intermediate ranges such as 5-10 wt %, 10-15 wt %, 15-20 wt %, 20-25 wt %, 25-30 wt % or any combination thereof. The fibrinogen solution may preferably be based on physiologically acceptable fluids such as water, physiological saline, balanced salt solutions, aqueous dextrose, glycerol or the like and comprised additional factors.

In one embodiment the fibrinogen solution comprises additionally Factor XIII. After conversion of the fibrinogen into fibrins, Factor XIII may support the fibrin sealant function by stabilizing and cross-linking fibrin alpha and gamma chains.

In one embodiment the fibrinogen solution comprises additionally an antifibrinolytic factor, preferably aprotinin. After dispensing of the fibrin sealant onto a desired site endogenous fibrinolysis e.g. mediated by plasmins may lead to a partial dissolution of the newly formed fibrin clot. The addition of antifibrinolytic factors such as aprotinin to the fibrinogen solution aids in delaying fibrinolysis.

In one embodiment the fibrinogen solution comprises in addition calcium chloride. Calcium chloride allows for the provision of $Ca^{2+}$ ion which augment cleavage activity of fibrinogen-cleaving proteases such as thrombin.

In another embodiment the container is filled with freeze-dried fibrinogen. Freeze-dried fibrinogen may be readily reconstituted to a fibrinogen solution by adding appropriate solutions. For example, the freeze-dried fibrinogen can be reconstituted using, a saline solution containing aprotinin, calcium chloride and/other additives. In preferred embodiments, Factor XII is provided in the container in a freeze-dried form or added upon reconstitution.

In a further aspect, the invention relates to a method for generating and dispensing a sealant to a desired site, comprising
   providing a dispenser, comprising
      a container filled with a fibrinogen solution, and
      an activation compartment,
   the activation compartment being situated downstream of the container and comprising a functionalized support to which a coagulation factor, preferably thrombin, is electrostatically immobilized, and
   dispensing the fibrinogen solution to the desired site, wherein upon dispensing, the fibrinogen solution passes through the activation compartment, thereby generating and dispensing polymerizing fibrin as a sealant.

In preferred embodiments the method may relate to generating and dispensing a sealant to a desired site for hemostasis. It may be particular preferred to employ the method in-situ in a subject in need for hemostasis, for instance in a subject undergoing surgery. The method is particularly beneficial for minimally invasive surgical procedures in which fast and precise hemostasis is essential for adequate visualization of the surgical field.

However, the method may also be employed ex-situ for instance for sealing or combining of components in medical implants and/or devices. The method may also be employed in non-medical settings, wherein the properties of the polymerizing fibrin to form a sealant can be advantageously exploited.

In a further aspect, the invention relates to a support for use in an activation compartment of a dispenser, wherein the support is a functionalized resin, preferably an amino-functionalized resin, comprising particles with a mean size of in between 150 and 300 μm to which a coagulation factor, preferably thrombin, is electrostatically immobilized.

In one embodiment the invention relates to a support for use in an activation compartment of a dispenser, producible by a method comprising:
   providing a functionalized support, which is a functionalized resin, preferably an amino-functionalized resin, comprising particles with a mean size of in between 150 and 300 μm,
   providing a solution comprising a coagulation factor, preferably thrombin, and incubating the solution comprising a coagulation factor with the functionalized support.

The support is preferably provided in a form that allows for an easy installation into an activation compartment of a dispenser as described herein. For instance, the support may be a functionalized resin, which can be readily shaped and dimensioned to fit into an activation compartment of the dispenser.

The method for producing of the functionalized support is simple and results in high immobilization yields of the coagulation factor, preferably thrombin. In some embodiments it may be preferred to employ a washing step of the functionalized resin prior to incubation, for instance with phosphate buffered saline (PBS). Optimal incubation can be achieved with concentrations of the coagulation factor, preferably thrombin, in said solution of in between 1 mg/mL and 100 mg/mL, preferably 10 mg/mL and 50 mg/mL. Preferred incubation times are more than 1 hour, preferably more than 3, 6, 12 hours and less than 48 hours, preferably less than 36 hours, 24 hours.

In one embodiment the invention relates to an exchangeable tip for use in a dispenser as described herein, wherein the exchangeable tip comprises an activation compartment comprising a functionalized support to which a coagulation factor is electrostatically immobilized and means for a releasable attachment to a main body of a dispenser.

The means for a releasable attachment to a main body of a dispenser may relate to any releasable attachment means such as threaded fasteners, bayonet mounts, snap fasteners, clamps, clips or the like.

In one embodiment the invention relates to a use of a dispenser, a support and/or an exchangeable tip as described herein for dispensing a sealant to a desired site, preferably for hemostasis.

In one embodiment the invention relates to a kit comprising
a dispenser, a support and/or an exchangeable tip,
a solution comprising fibrinogen, and
optionally instructions for a method for dispensing a sealant, preferably for hemostasis.

Technical features that have been disclosed for the dispenser as described herein also apply for the support, exchangeable tip, the method and/or the kit. A person skilled in the art recognizes that preferred features of the dispenser as described herein can be advantageously employed in the context of the support, exchangeable tip, method and/or the kit and convey the same beneficial effects.

DETAILED DESCRIPTION OF THE INVENTION

The invention relates to a dispenser of a sealant for hemostasis comprising a container for receiving a fibrinogen solution and an activation compartment, in which a coagulation factor, preferably thrombin, is immobilized. The invention further relates to a support for use in the activation compartment, an exchangeable tip comprising the activation compartment as well as methods and a kit for generating and dispensing a sealant.

As is evident from the data presented herein, the immobilization of the coagulation factor on a functionalized support in the activation compartment allows for dispensing effectively polymerizing fibrin as a sealant, while minimizing coagulation factor release into the site of deposition.

The present invention has the following advantages over conventional dispensers: the inventive dispenser, components, methods and the kits are fast, easy to use, reliable and precise for dispensing a sealant to a desired site in particular for hemostasis.

As used herein "hemostasis" refers to the process of stopping the bleeding of potentially damaged tissues or blood vessels and thus preventing hemorrhage. Hemostasis is the first stage of wound healing and involves the coagulation of blood to impede further bleeding. The dispenser of the present invention allows for the deposition of a fibrin sealant that efficiently promotes hemostasis as well as wound healing and is readily absorbable.

Endogenous wound healing as natural process begins almost instantly after injury and requires the successive coordinated function of a variety of cells and the close regulation of degradative and regenerative steps. The proliferation, differentiation and migration of cells are important biological processes which underlie wound healing, which also involves fibrin clot formation, resorption of the clot, tissue remodelling, such as fibrosis and endothelialization. Wound healing involves the formation of highly vascularized tissue that contains numerous capillaries, many active fibroblasts, and abundant collagen fibrils. The process of wound healing can be initiated by thromboplastin which flows out of injured cells and plasma factor VII to form factor X activator, which then, with factor V and in a complex with phospholipids and calcium, converts prothrombin into thrombin. Thrombin catalyzes the release of fibrinopeptides A and B from fibrinogen to produce fibrin monomers (viz. fibrin I and fibrin II), which aggregate to form fibrin filaments. Thrombin also activates the transglutaminase, factor XIIIa, which catalyzes the formation of isopeptide bonds to covalently cross-link the fibrin filaments.

The device of the present invention allows for application of a tissue sealant that supports hemostasis and promotes wound healing. Surgical adhesives and tissue sealants which contain plasma proteins are routinely used for sealing internal and external wounds to reduce blood loss and maintain hemostasis. Typically tissue sealants contain blood clotting factors and other blood proteins.

As used herein the "sealant" is preferably a fibrin sealant. A fibrin sealant is a gel similar to a natural clot which is prepared from plasma. The precise components of fibrin sealants are a function of the particular plasma fraction which is used as a starting material. Fractionation of plasma components can be effected by standard protein purification methods. Such as ethanol, polyethylene glycol, and ammonium sulfate precipitation, ion exchange, and gel filtration chromatography. Typical fibrin sealants contain a mixture of proteins including traces of albumin, fibronectin and plasminogen, some also contain aprotinin as a stabilizer.

"Fibrinogen" used in the practice of this invention includes any fibrinogen that will form fibrin in a human body.

"Fibrinogen solution" refers to an aqueous solution comprising substantial amounts of fibrinogen and optionally further amounts of other factors stimulating fibrin formation, when in contact with the immobilized activation compound, preferably thrombin such that fibrin formation and cross-linking takes place conferring on the composition the properties of a tissue sealant. The fibrinogen solution may be based on physiologically acceptable fluids such as water, physiological saline, balanced salt solutions, aqueous dextrose, glycerol or the like. The fibrinogen solution may alternatively or in addition comprise further substances to optimize reaction conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate.

Frequently, fibrinogen is provided in freeze-dried form, and reconstituted to form a fibrinogen solution prior to use. The fibrinogen can also be frozen or fresh, autologous (from the subject to be treated), human including pooled human fibrinogen, recombinant, and bovine or other non-human source such as fish (e.g., salmon and sea trout). Freeze-dried fibrinogen may be reconstituted using a solution, typically containing aprotinin and calcium chloride. The fibrinogen may be reconstituted with a solution that includes at least one additive. For example, the freeze-dried fibrinogen can be reconstituted using, for example, saline with an anesthetic or an additive, a saline solution containing aprotinin and an anesthetic or an additive, a saline solution containing anesthetic, optionally an additive, and calcium ions ($Ca^{+2}$) such as may be supplied from calcium chloride, or a solution containing combinations of anesthetic, antibiotics or other and/or additives.

Fibrinogen may be in an intimate admixture with other proteins that are typically found in anti-coagulated, whole blood, in platelet-rich plasma, in plasma, in cryoprecipitate, or in precipitates of plasma obtained by a method such as Cohn precipitation of plasma. Such additional protein components may include fibronectin, immunoglobulin, particularly IgG, factor XIII, plasminogen, and albumin. The fibrinogen solution envisioned herein can be virally inactivated by one or more methods prior to their employment in the invention.

Alternative sources of human fibrinogen may also be envisioned. For example, fibrinogen made by recombinant techniques could also be employed in the fibrin sealant. Molecular techniques available for the production of recombinant fibrinogen include the use of COS-1 or Hep G2 cells transfected with DNA vectors containing isolated genes encoding normal or mutant human fibrinogen (Roy S. N. et al., 1991, J. Biol. Chem., 266:4758-4763).

The term "coagulation factor" as used herein denotes a blood coagulation factor or blood clotting factor, which acts by cleaving downstream proteins in the coagulation pathway. Preferably the coagulation-factor is thus a "fibrinogen-cleaving protease", which converts soluble fibrinogen into insoluble strands. Most preferably the coagulation factor is thrombin.

As used herein, the term "thrombin" refers to the serine protease that converts soluble fibrinogen into insoluble strands of fibrin and catalyzes a number of other coagulation-related reactions. This term is not species-specific unless otherwise designated. The term encompasses α-thrombin, which is the native form of thrombin, as well as γ-thrombin, a non-clotting derivative produced from α-thrombin that retains much of its platelet-activating capacity. Thrombin is a common physiological instigator of clotting. Thrombin from a number of mammalian sources, most commonly bovine, is routinely used in commercially-available fibrin sealants.

Both fibrinogen and thrombin may be derived from blood plasma by the fractionation of plasma. Comprehensive reviews on the preparative techniques of each have been published and are the basis for most commercial plasma fractionation procedures used by those skilled in the art and suitable for use in the invention (For fibrinogen: Blomback, B. and Blomback, M., 1956, Ark Kemi, 10:415-443; Stryker, M. H. & Waldman, A. A., 1978, Kirk-Othmer Encyclopedia of Chemical Technology, Vol 4, 3rd ed., pp 25-61, John Wiley; Lowe G. D. O. et al., 1987, Fibrinogen 2: Biochemistry, Physiology and Clinical Relevance. Excerpta Medicus, Elsevier Science Publishers; For thrombin: Fenton I I, J. W. et al., 1977, J. Biol. Chem., 252:3587-3598; Gaffney P. J. et al., 1992, Thrombos. Haemostas., 67:424-427; Ward, G., 1991, European Patent Application No. EP 0 439 156 A1; and U.S. Pat. No. 5,143,838 to Kraus et al.).

The expression "support" as used herein refers to the portion of a matrix which serves as the "substrate" or "support material" to which the coagulation factor, preferably thrombin is immobilized. A suitable support according to the present invention should be hydrophilic as well as mechanically and chemically stable over the relevant pH range and temperature.

Preferably the support is a resin. The expression "resin" as used herein, refers to an insoluble material comprising polymeric particles, typically in the form of spheroidal beads, or pearls, which may be formed by suspension polymerization methods well-known to the art. The particles of the resin may thus also be referred to as resin particles.

Such resins can be natural or bio-polymers, synthetic polymers and inorganic materials. Agarose, dextrose and cellulose beads are commonly employed natural supports. Synthetic polymeric or organic supports are mostly based on acrylamide, polystyrene and polymethacrylate derivatives, whereas, porous silica and glass are some frequently used inorganic supports. Other materials which can be used in accordance with the invention are described below.

As used herein, the term "polymer" refers to a molecule composed of repeating structural units typically connected by covalent chemical bonds. The term "polymer" is also meant to include the terms copolymer and oligomers.

According to one embodiment of the invention, the resin is composed of polymers selected from the group consisting of alginate, chitosan, chitin, collagen, carrageenan, gelatin, cellulose, starch, pectin and sepharose; inorganic materials selected from the group consisting of zeolites, ceramics, celite, silica, glass, activated carbon and char-coal; or synthetic polymers selected from the group consisting of polyethylene (PE), polyoxymethylene (POM), polypropylene (PP), polyvinylchloride (PVC), polyvinyl acetate (PVA), polyvinylidene chloride (PVDC), polystyrene (PS), polytetrafluoroethylene (PTFE), polyacrylate (PAA), polymethyl methacrylate (PMMA), polyacrylamide, polyglycidyl methac-rylate (PGMA), acrylonitrile butadiene styrene (ABS), polyacrylonitrile (PAN), polyester, polycarbonate, polyethylene terephthalate (PET), polyamide, polyaramide, polyethylene glycol (PEG), polyvinylpyrrolidone (PVP), polysulfone (PS), polyethersulfone (PES), polyarylethersulfone (PEAS), eth-ylene vinyl acetate (EVA), ethylene vinyl alcohol (EVOH), polyamideimide, polyaryletherketone (PAEK), polybutadiene (PBD), polybutylene (PB), polybutylene terephthalate (PBT), polycaprolactone (PCL), polyhydroxyalkanoate, polyether ether ketone (PEEK), polyether ketone ketone (PEKK), polyether imide (PEI), polyimide, polylactic acid (PLA), polymethyl pentene (PMP), poly(p-phenylene ether) (PPE), polyurethane (PU), styrene acrylonitrile (SAN), polybutenoic acid, poly(4-allylbenzoic acid), poly(glycidyl acrylate), polyglycidyl methacrylate (PGMA), acrylonitrile butadiene styrene (ABS), polydivinylbenzene (PDVB), poly(allyl glycidyl ether), poly(vinyl glycidyl ether), poly(vinyl glycidyl urethane), polyallylamine, pol-yvinylamine, copolymers of said polymers and any of these polymers modified by introduction of functional groups. According to one specific embodiment of the invention, the support is selected from the group consisting of styrene divinylbenzene (DVB) and derivatives, polymethyl methacrylate (PMMA) and derivatives, and polyglycidyl methacrylate (PGMA) and derivatives.

Most preferably the resin is composed of methacrylate polymers, preferably polymethyl methacrylate (PMMA).

Preferably the resin is a porous resin. In some embodiments the resin may be a macroporous, mesoporous or gel-type resin.

The term "pore" as used herein refers to a depression, slit, or hole of any size or shape in the particles as solid objects. A pore can run all the way through the particle or partially through the particle. A pore can intersect other pores.

The term "macroporous" (also referred to as macroreticular) is well-known in the art and, in general, refers to resins prepared from copolymer beads which have regions of densely packed polymer chains exhibiting molecular-sized porosity which are separated by copolymer-free voids, often referred to as mesopores (50-200 Å) and macropores (>200 Å). In contrast, microporous, or gel-type, resins have pores generally of molecular-size (generally less than about 50 Å) and are prepared from monomer mixtures which do not employ an inert diluent. Macroporous and gel resins are further described in U.S. Pat. Nos. 4,224,415 and 4,382,124, the teachings of which are incorporated herein by reference.

The "particle size" or "resin size" preferably refers to the characteristic dimension of the polymeric particles that make up the resin. In case of polymeric beads the particle size preferably relates to the bead diameter.

In general, functionalized resins, such as ion-exchange resins, comprise a plurality of polymeric particles formed by suspension polymerization methods and have a plurality of attached functional groups which are capable of retaining ions, or molecules, of proteins, such as a coagulation factor, when in contact with a liquid containing such a protein. The nature of a suspension polymerization process is such that the resulting copolymer beads may exhibit differing particle sizes, i.e., the beads collectively fit into a distribution of particle sizes. This distribution is retained, and in most instances widened, when the copolymer beads are substantially functionalized with functional groups.

The "mean of the particle size" preferably relates to the arithmetic mean, while the "standard deviation of particle size" preferably quantifies the variation of particles sizes present in the resin.

The mean of the particle size and standard deviation for a given resin, or sample of copolymer beads or resin particles may be determined using any commercially available instrument designed to measure the particle size distribution of a discrete particle sample. Examples of such instruments are the particle size analyzers available from Shimadzu or Horiba.

There are several types of supports as mentioned above and below that can be advantageously utilized to immobilize proteins such as a coagulation factor, preferably. Supports can be based on materials such as polysaccharide. Suitable polysaccharides are, for example, cellulose, nitrocellulose, chitosan, collagen, starch and cross-linked polysaccharide gels such as agarose, Sephadex or Sepharose. Methods for preparing derivatives of polysaccharide matrices have long been known and are, for example, described in U.S. Pat. Nos. 4,411,832 or 3,947,352. The supports can also be based on synthetic organic supports. Synthetic polymeric matrices comprise hydrophilic and hydrophobic synthetic polymers and combinations thereof. Synthetic supports comprise supports selected, for example, from the group of supports consisting of polyacrylamide supports or derivatives thereof; polymethacrylate supports or derivatives thereof; polystyrene supports or derivatives thereof; or polyether-sulfone supports or derivatives thereof. Otherwise, derivatized silica, glass or azlactone beads can be used in devices according to the invention. Such devices preferably make use of organic supports. The use of beads is particularly advantageous in the context of the present invention.

A functionalized support, preferably a functionalized resin refers to a support, preferably a resin, that comprises functional groups allowing for the immobilization or binding of the coagulation factor.

The expression "immobilizing", "binding" or coupling of a coagulation factor to the support, preferably a resin, for providing an activation compartment for use in the invention refers to a non-covalent or electrostatic binding that hold molecules together. Non-covalent or electrostatic immobilization may be used synonymous and include, but are not limited to, hydrogen bonding, metal ion-binding, ionic interactions among charged groups, van der Waals interactions, and hydrophobic interactions among non-polar groups.

One or more of these interactions can mediate the immobilization of the coagulation factor to the functionalized support, preferably resin. The binding may otherwise be specific or selective, or unspecific.

The immobilization can be carried out via common functional groups, including amines, alcohols, carboxylic acids, aldehydes and epoxy groups. Methods of preparing supports are known in the art and are described, for example, in U.S. Pat. No. 8,142,844 B2, US 2015/0111194 A1 and US 2014/0166580 A1. These references also describe spacer groups (or "linker" groups) which can be used in generating a functionalized support.

However, for use in the invention functional groups mediating a non-covalent or electrostatic interaction under certain conditions are particularly preferred.

For instance it is particularly preferred to use an amino-functionalized resin that comprises amino groups that can be used for protein immobilization by ionic interaction of the ionizable surface aminoacids (e.g. Lys, Arg, His, Asp, Glu) with the charged amines on the polymer.

Such amino-functionalized resin may also be pre-activated, e.g. by glutaraldehyde and to provide reactive groups for forming covalent linkages. However, as described above an electrostatic immobilization, e.g. based on an ionic interaction has been found to be particularly suited to maintain high protein activity. Therefore, when using amino-functionalized resins the immobilization of the coagulation factor will be preferably carried out under such conditions that an electrostatic binding instead of a covalent binding is achieved. To this end for instance a pH adjustment during the immobilization reaction may be required.

Many functionalized resins are commercially available and known to a person skilled in the art which are suited for an electrostatic immobilization of a protein such as a coagulation factor. Particularly preferred examples include Purolite® Lifetech™ methacrylate polymers functionalized with amino groups, wherein different spacer moiety may be chosen. However also other specific functional resins may be envisioned e.g. Purolite® Lifetech™ octadecyl methacrylate, macroporous styrene or DVB/methacrylate for mediating protein absorption as well as styrene tertiary amine or styrene quaternary amine for mediating an ionic immobilization.

According to one aspect, Purolite® Lifetech™ ECR8409F amino methacrylate beads are used as a functionalized resin which carry an amino group as a functional group to which a coagulation factor, such as thrombin can be electrostatically immobilized. They have a particle size of in between 150 and 300 µm, with a mean particle size of 198

μm, a pore diameter of in between 600 and 1200 Å (mean pore size: 805 Å) and a hexamethylene (C6) spacer moiety.

As used herein the term "amino-functionalized resin" or "amino-terminated resin" refers to a resin comprising amino or amine groups as functional groups for electrostatically immobilizing proteins such as a coagulation factor.

The term "amino group" or "amine group" is preferably used herein to refer to the group $-NZ^1Z^2$, where each of $Z^1$ and $Z^2$ is independently selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "primary amino group" is used herein to refer to $-NH_2$, which is a most preferred amino group.

The term "secondary amino group" is used herein to refer to $-NZ^1H$, where $Z^1$ is selected from the group consisting of alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "tertiary amino group" is used herein to refer to $-NZ^1Z^2$, where each of $Z^1$ and $Z^2$ is independently selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "quaternary amino group" is used herein to refer to $-NZ^1Z^2, Z^{3+}$, where each of $Z^1$, $Z^2$ and $Z^3$ is independently selected from the group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

Further preferred functional resins may be chosen from known ion-exchange resins which are commercial available at a high variety. As used herein, the term "ion exchange resin" is meant to refer to its conventional meaning, namely a resin comprising crosslinked polymer beads and a functional group which makes it suitable for use in an ion exchange process.

Ion exchange is a well known, commercially practiced process and is widely reported in the open literature. A review of ion exchange technology is given in "Kirk-Othmer Cyclopedia of Chemical Technology" (3rd ed., Vol. 13, p. 678-705, by R. M. Wheaton and L. J. Lefevre, published by Wiley and Sons). As disclosed in the aforesaid Kirk-Othmer reference, conventional ion exchange resins normally have sulfonic acid functionality, but it is known to prepare ion exchange resins having other types of functional groups.

Ion exchange comprises a reversible chemical reaction wherein an ion in a fluid medium is exchanged for a similarly charged ion attached to an immobile solid particle that is insoluble in the fluid medium. The term ion exchange resin is used to refer to such substances. The resin is rendered insoluble due to the crosslinked nature of the polymeric support to which the ion exchanging groups are attached. Ion exchange resins are classified as acidic, cation exchangers, which have positively charged mobile ions available for exchange, and basic, anion exchangers, whose exchangeable ions are negatively charged.

Both acidic, cation exchange resins and basic, anion exchange resins can be employed in the instant invention for immobilizing the coagulation factor. In one embodiment, the acidic, cation exchange resin comprises an organic acid, cation exchange resin, such as a sulfonic acid cation exchange resin. Sulfonic acid cation exchange resins contemplated for use in the practice of the invention can comprise at least one member selected from the group consisting of sulfonated styrene-divinylbenzene copolymers, sulfonated crosslinked styrene polymers, phenol-formaldehyde-sulfonic acid resins, benzene-formaldehyde-sulfonic acid resins, and mixtures thereof.

In another embodiment, the acidic, cation exchange resin comprises at least one organic acid, cation exchange resin, such as carboxylic acid, acrylic or phosphoric acid cation exchange resin and mixtures thereof. In addition, mixtures of different cation exchange resins can be used. In many cases, the basic ion exchange resin can be used to adjust the pH to the desired level in order to ensure an electrostatic immobilization of the coagulation factor. In some cases, the pH can be further adjusted with an aqueous basic solution such as a solution of sodium hydroxide, ammonium hydroxide, tetra-methylammonium hydroxide, calcium hydroxide, cesium hydroxide, and mixtures thereof, among others.

Commercially available cation exchange resins include, but are not limited to, for example, those having a sulfonate based group (e.g., MonoS, MiniS, Source 15S and 30S, SP Sepharose Fast Flow™, SP Sepharose High Performance from GE Healthcare, Toyopearl SP-650S and SP-650M from Tosoh, Macro-Prep High S from BioRad, Ceramic HyperD S, Trisacryl M and LS SP and Spherodex LS SP from Pall Technologies,); a sulfoethyl based group (e.g., Fractogel SE, from EMD, Poros S-10 and S-20 from Applied Biosystems); a sulphopropyl based group (e.g., TSK Gel SP 5PW and SP-5PW-HR from Tosoh, Poros HS-20 and HS 50 from Applied Biosystems); a sulfoisobutyl based group (e.g., (Fractogel EMD SO3 "from EMD); a sulfoxyethyl based group (e.g., SE52, SE53 and Express-Ion S from Whatman), a carboxymethyl based group (e.g., CM Sepharose Fast Flow from GE Healthcare, Hydrocell CM from Biochrom Labs Inc., Macro-Prep CM from BioRad, Ceramic HyperD CM, Trisacryl M CM, Trisacryl LS CM, from Pall Technologies, Matrx Cellufme C500 and C200 from Millipore, CM52, CM32, CM23 and Express—Ion C from Whatman, Toyopearl CM-650S, CM-650M and CM-650C from Tosoh); sulfonic and carboxylic acid based groups (e.g. BAKEPVBOND Carboxy-Sulfon from J. T. Baker); a carboxylic acid based group (e.g., WP CBX from J. T Baker, DOWEX MAC-3 from Dow Liquid Separations, Amberlite Weak Cation Exchangers, DOWEX Weak Cation Exchanger, and Diaion Weak Cation Exchangers from Sigma-Aldrich and Fractogel EMD COO—from EMD); a sulfonic acid based group (e. g., Hydrocell SP from Biochrom Labs Inc., DOWEX Fine Mesh Strong Acid Cation Resin from Dow Liquid Separations, UNOsphere S, WP Sulfonic from J. T. Baker, Sartobind S membrane from Sartorius, Amberlite Strong Cation Exchangers, DOWEX Strong Cation and Diaion Strong Cation Exchanger from Sigma-Aldrich); and a orthophosphate based group (e.g., PI 1 from Whatman).

In another embodiment, the basic, anionic exchange resin comprises at least one tertiary amine anion exchange resin. Tertiary amine anion exchange resins contemplated for use in the practice of the invention can comprise at least one member selected from the group consisting of tertiary-aminated styrene-divinylbenzene copolymers, tertiary-aminated crosslinked styrene polymers, tertiary-aminated phenol-formaldehyde resins, tertiary-aminated benzene-formaldehyde resins, and mixtures thereof. In a further embodiment, the basic, anionic exchange resin comprises at least one quaternary amine anion exchange resin, or mixtures of these and among other exchange resins.

Commercially available anion exchange resins include DEAE cellulose, Poros PI 20, PI 50, HQ 10, HQ 20, HQ 50, D 50 from Applied Biosystems, Sartobind Q from Sartorius, MonoQ, MiniQ, Source 15Q and 30Q, Q, DEAE and ANX Sepharose Fast Flow, Q Sepharose high Performance, QAE SEPHADEX™ and FAST Q SEPHAROSE™ (GE Healthcare), WP PEI, WP DEAM, WP QUAT from J. T. Baker, Hydrocell DEAE and Hydrocell QA from Biochrom Labs Inc., UNOsphere Q, Macro-Prep DEAE and Macro-Prep High Q from Biorad, Ceramic HyperD Q, ceramic HyperD DEAE, Trisacryl M and LS DEAE, Spherodex LS DEAE, QMA Spherosil LS, QMA Spherosil M and Mustang Q from Pall Technologies, DOWEX Fine Mesh Strong Base Type I and Type II Anion Resins and DOWEX MONOSPHER E 77, weak base anion from Dow Liquid Separations, Intercept Q membrane, Matrex Cellufme A200, A500, Q500, and Q800, from Millipore, Fractogel EMD TMAE, Fractogel EMD DEAE and Fractogel EMD DMAE from EMD, Amberiite weak strong anion exchangers type I and II, DOWEX weak and strong anion exchangers type I and II, Diaion weak and strong anion exchangers type I and II, Duolite from Sigma-Aldrich, TSK gel Q and DEAE 5PW and 5PW-HR, Toyopearl SuperQ-650S, 650M and 650C, QAE-550C and 650S, DEAE-650M and 650C from Tosoh, QA52, DE23, DE32, DE51, DE52, DE53, Express-Ion D and Express-Ion Q from Whatman.

Preferred functionalized resin may be chosen from the above-mentioned ion-exchange resins or other commercially available ion-exchange resins by selecting resins with a mean particle size of in between 150 μm and 300 μm and a functionalization that allows for an electrostatic immobilization of a coagulation factor, preferably thrombin.

According to one preferred embodiment the support comprises a spacer moiety to which a functionalized group is attached that may mediate the electrostatic immobilization.

The terms "spacer moiety," "linkage" or "linker" are used herein to refer to an atom or a collection of atoms optionally used to link, e.g. by covalent attachment, the functional group to the polymeric particles of the resin. The spacer moiety or linker may be hydrolytically stable or may include a physiologically hydrolyzable or enzymatically degradable linkage. A linker, as used herein, is not a single covalent bond. The structure of the linker is not crucial, provided it yields a physical separation of the functional group from the surface of the polymeric particles of the resin.

In certain embodiments, the spacer organic moiety comprising $C_2$-$C_{40}$, $C_2$-$C_{20}$ preferably $C_3$-$C_{10}$, preferably a branched or unbranched alkyl, alkenyl, alkynyl, aryl, aminoalkyl, aminoalkenyl, aminoalkynyl, heteroaryl, amide and/or aralkyl group, or combination thereof.

The term "alkyl" refers to a branched or unbranched saturated hydrocarbon group of preferably 1 to 24 carbon atoms, such as methyl, ethyl, n-propyl, isopropyl, w-butyl, isobutyl, f-butyl, pentyl, hexyl, heptyl, octyl, decyl, tetradecyl, hexadecyl, eicosyl, tetracosyl and the like. Preferred alkyl groups have 1 to 12 carbon atoms, 1 to 6 carbon atoms, more preferably 1 to 4 carbon atoms. Any one or more of the alkyl groups described herein may be "substituted alkyls", wherein one or more hydrogen atoms are substituted with a substituent such as halogen, cycloalkyl, alkoxy, amino, hydroxyl, aryl, or carboxyl.

The term "aryl" refers to any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

The term "alkoxy" is used herein to refer to the —OZ1 radical, where Z1 is selected from the group consisting of alkyl, substituted alkyl, cycloalkyl, substituted cycloalkyl, heterocylcoalkyl, substituted heterocycloalkyl, silyl groups and combinations thereof as described herein. Suitable alkoxy radicals include, for example, methoxy, ethoxy, benzyloxy, t-butoxy, etc. A related term is "aryloxy" where Z1 is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy and the like.

A "dispenser" as used herein refers to any device that allows for dispensing a fluid. Typically a dispenser will comprise a container configured for receiving said fluid as well as means for expelling the fluid from the container through an outlet or a tip situated downstream of the container. Preferred examples of dispenser are automatically or manually operatable syringes comprising a container, also referred to as a barrel, a plunger as a means for expelling the fluid, typically in form of a piston with a plug as well as a tip and/or needle for precise guidance and deposition of the fluid.

As used herein the "container configured to receive a fibrinogen solution" preferably refers to any receptacle suitable for receiving and holding of an aqueous solution such as a fibrinogen solution. The material of the container is not particular limited, preferably the material is waterproof. Examples of suitable materials include glass, plastic, preferably rigid plastic or other durable materials. In preferred embodiments the material is transparent, such that the colour and/or filling status of the fibrinogen solution is visible.

The shape of the container may be conical, cuboid or cylindrically. Preferred volumes range in between 0.1 ml to 100 ml, preferably 0.5 ml to 10 ml.

The activation compartment refers to a compartment of the dispenser configured for receiving and holding the support. The activation compartment is preferably in fluid communication with the container to allow for passage of the fibrinogen solution into the activation compartment upon dispensing.

In the context of the invention upstream and downstream relates to the direction of dispensing. In its typical mode of operation a fluid in the dispenser will upon dispensing hence first pass an upstream component before passing a downstream component.

The activation compartment and the container may be part of the same, preferably rigid, structure and preferably made from the same material to form a main body of the dispenser. The activation compartment and the container may be also situated in two separated, but attachable components. This is for instance the case, when the activation compartment is part of an exchangeable tip.

The activation compartment and the container may have any cross-sectional shape (circular, oval, triangular, irregular, square or rectangular, or the like). It is preferred however that that the activation compartment and container have similar cross-sectional shape and dimension at their contacting location.

As used herein a "tip" refers to the most downstream extrusion portion of a dispenser. At its dispensing end the tip typically exhibits a substantially reduced cross-sectional area compared to its more upstream end in order to allow for an accurate deposition of the sealant. The tip may be characterized by an at least partially conically shape and in preferred embodiment comprise a blunt-ended needle or a spray tip portion.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

Thus, the terms "comprising"/"including"/"having" mean that any further component (or likewise features, integers, steps and the like) can/may be present. The term "consisting of" means that no further component (or likewise features, integers, steps and the like) is present.

The term "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

Thus, the term "consisting essentially of" means those specific further components (or likewise features, integers, steps and the like) can be present, namely those not materially affecting the essential characteristics of the composition, device or method. In other words, the term "consisting essentially of" (which can be interchangeably used herein with the term "comprising substantially"), allows the presence of other components in the composition, device or method in addition to the mandatory components (or likewise features, integers, steps and the like), provided that the essential characteristics of the device or method are not materially affected by the presence of other components.

FIGURES

The present invention is further described by reference to the following figures. The figures exemplify non-limiting and potentially preferred embodiments, presented for further illustration of the invention.

FIG. 1 Activity of 20 µL of thrombin immobilized resin with epoxy (black) or amino (red and green) functionality, immobilization conditions were 20 mg/mL thrombin and resin:buffer ratio of 1:2. Solid lines represent raw data, while the underlying dashed lines depict corrected values after subtracting fluorescence signal from unmodified resins (bottom dashes lines).

Figure 2:
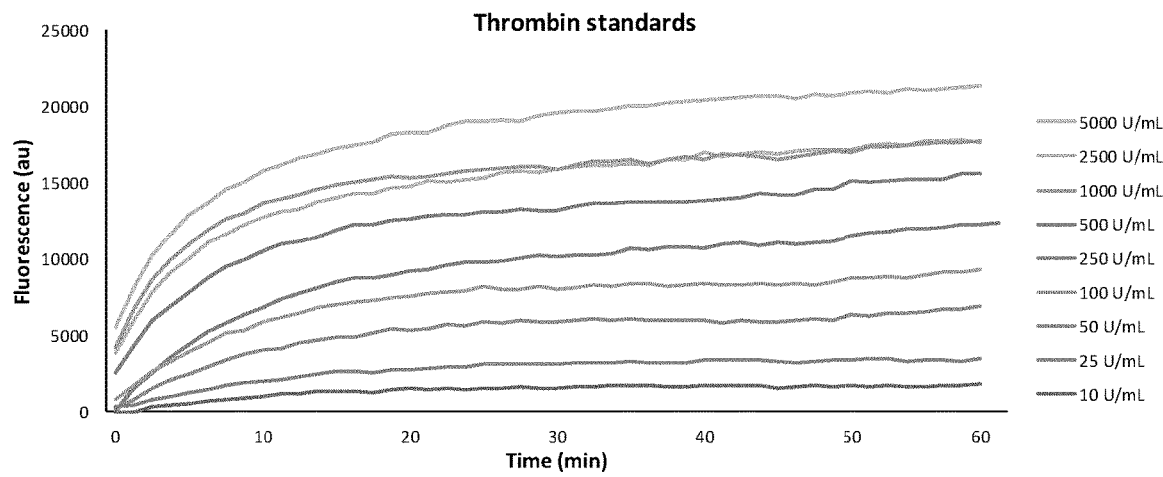

FIG. 2 Thrombin activity of typical standards used in fluorescence experiments.

Figure 3:
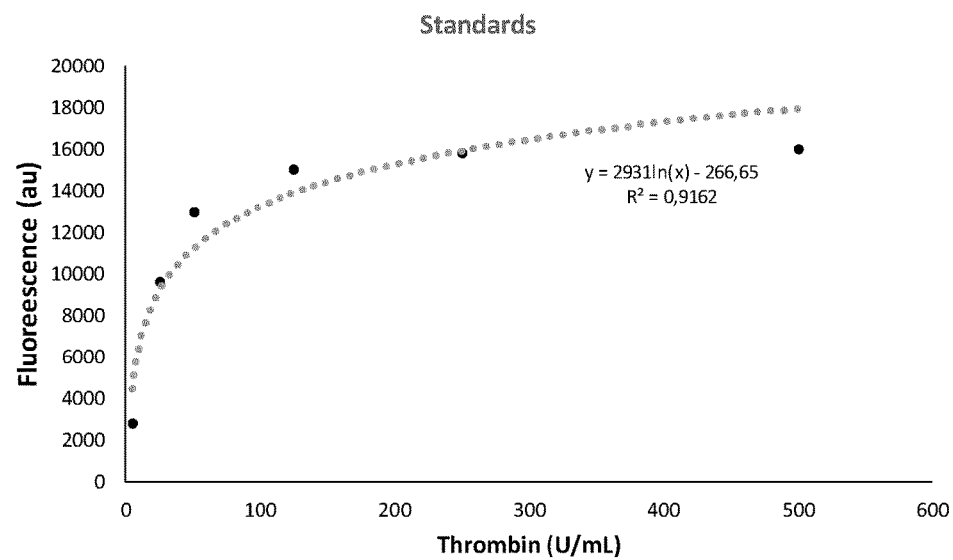

FIG. 3. Fluorescent signal of standards after 60 min, including the regression line used to calculate the apparent activity of immobilized thrombin.

Figure 4:
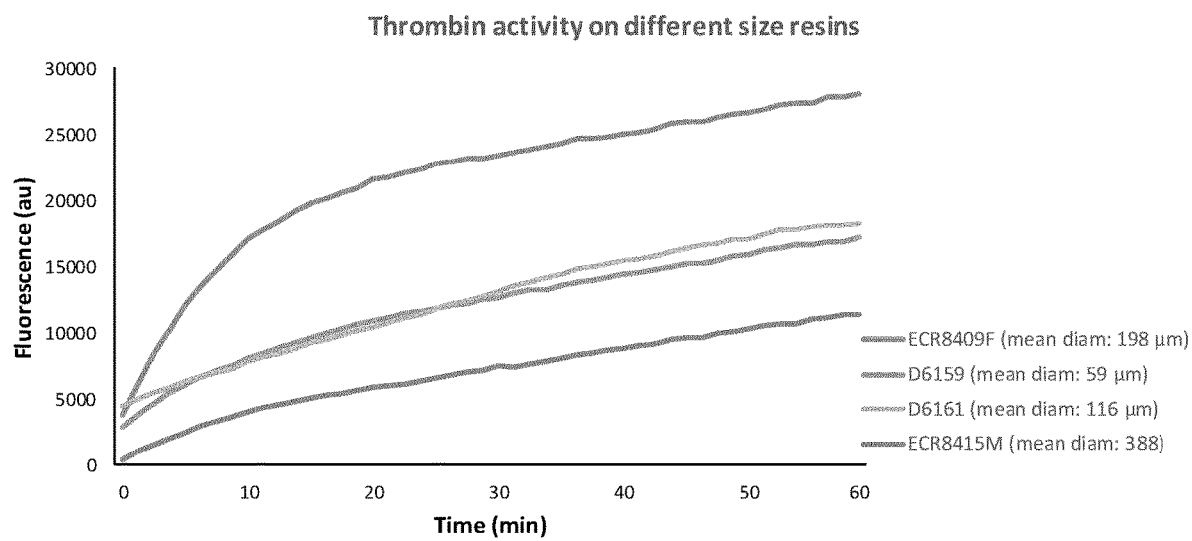

FIG. 4. Activity of thrombin immobilized on amino-terminated resins with different mean diameters.

Figure 5:
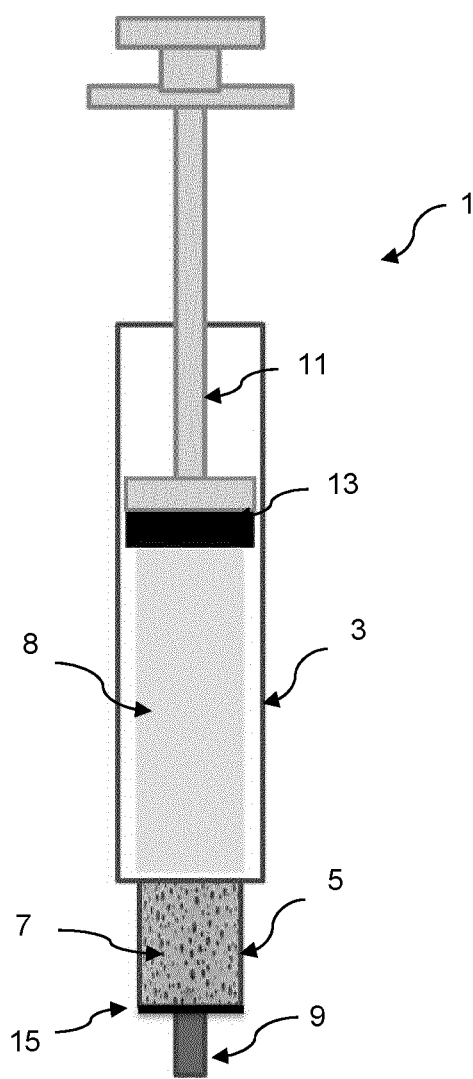

FIG. 5 Schematic representation of a preferred embodiment of a dispenser.

EXAMPLES

The present invention is further described by reference to the following non-limiting examples. The examples describe non-limiting and practical embodiments, presented for further illustration of the invention.

Methods of the Examples

Thrombin Immobilization.

Epoxy-(no spacer) and amino-(long C6 spacer) functionalized resins (Purolite GmbH Ratingen, Germany) with a pore size of 600-1200 Å (mean pore size: 879 Å and 805 Å, respectively) and a diameter of 150-300 µm (mean diameter: 222 µm and 198 µm, respectively) were equilibrated by washing with an excess of phosphate buffered saline (PBS) (Lonza Verviers, Belgium,) using a glass filter and moderate negative pressure. After three washing steps, the resins were added to separate 10-50 mg/mL solutions of thrombin (Bio-Pharm Laboratories LLC Bluffdale, USA) in PBS, at a resin:buffer ratio of 1:2-4, and left on a tumbler shaker overnight at RT. After immobilization, the immobilization solution was examined using a Pierce BCA assay kit (Thermo Fisher Scientific GmbH Dreiech, Germany) to determine the immobilization yield. The resin was washed three times using 50 mL PBS, once with 50 mL 0.5 M NaCl and with 50 mL PBS, and stored in PBS at a resin:buffer ratio of 1:2. The collected wash solution was saved and used to determine final immobilization yield.

Thrombin Activity.

The activity of the immobilized thrombin was determined using a fluorogenic thrombin substrate (Benzoyl-Phe-Val-Arg-AMC·HCl, Merck GmbH Darmstadt, Germany) and compared to standard amounts of thrombin. Briefly, the tip of a standard 200 µL pipette tip was cut off at approximately 5 mm from the end to enlarge the opening, and 20 µL of resin suspension was pipetted into a black flat well 96-well plate (Nunc Thermo Fisher Scientific GmbH Dreiech, Germany). To the same well, 30 µL of PBS was added, while from each thrombin standard (0-500 U/mL) 50 µL was added to the 96-well plate. As a control, and to determine the background fluorescence signal, 20 µL of unmodified resin together with 30 µL of PBS were added to the plate as well. When each well contained a total of 50 µL liquid (standards), or liquid resin mixture (immobilized thrombin), 100 µL of 1 mM thrombin substrate was added, the plate was immediately transferred to the plate reader (Fluostar Optima, BMG Labtech GmbH Ortenberg, Germany) and the measurement was started. Fluorescence was measured using excitation and emission wavelengths of 350 nm and 430 nm, respectively. The fluorescence signal was measured every 150 s for 1 h.

Fibrinogen Activation and Gel Formation.

200 µl of thrombin immobilized resin was suspended in 200 µl of 0.4 M $CaCl_2$, after 5 min, the resin was added to a modified syringe tip containing a 1.5 µm pore filter. A 1 mL syringe was used to aspirate 500 µl solution of 90 mg/mL fibrinogen (Merck GmbH, Darmstadt, Germany) in ultra-pure $H_2O$, and the syringe was connected to the tip containing the resin. The fibrinogen solution was then forced through the tip containing the thrombin immobilized resin onto a glass microscope slide and gel formation was observed within 1 min.

Example 1: Immobilization Yield for Thrombin

Immobilization yield was determined using 500 mg of amino-terminated resin in 2 mL of PBS with varying thrombin concentrations. Initial yield was calculated by determining the protein content of immobilization solutions, while the final yield included the amount of thrombin lost after washing.

Table 1 exhibits the yield and final yield of thrombin immobilization on amino-terminated resins and demonstrate that for these resin high yields can be obtained for different thrombin concentrations.

Example 2: Determination of Thrombin Activity

Activity of thrombin was determined for epoxy- and amino-terminated resins (FIG. 1), while in the case of amino-terminated resin both low (technical grade) and high purity thrombin (technical: 90-250 U/mg, high purity: >1500 U/mg) were used. Activity of thrombin immobilized on epoxy-terminated resins was lowest, and resulted in an increasing fluorescence signal during the time of the measurements, reaching a maximum of approximately 10000 au. When immobilized on amino-terminated resins, thrombin activity was considerably higher and increased exponentially during the first minutes of the measurement, before continuing linearly after 30 min. In the case of technical grade thrombin, the maximum values obtained were around 20000 au, while the use of high purity thrombin resulted in values exceeding 25000 au.

To compare the activity of immobilized thrombin to the activity of free thrombin, several standards were included in each experiment (FIG. 2).

Apparent thrombin activity of immobilized thrombin was calculated using thrombin standards and the obtained fluorescent signal after 60 min.

Table 2 shows the results for apparent activity of immobilized thrombin for different resin types. Particular good results were obtained for amino-terminated resins, in particular in case of high thrombin grade.

Activity of thrombin was also determined for amino-terminated resins with different mean diameter of the resin particles (FIG. 4). Activity of thrombin immobilized on a resin with a mean diameter of 388 μm was lowest, and resulted in slow linear fluorescence signal increase during the time of the measurements, reaching a maximum of approximately 7000 au. When using resins with mean particles sizes of 59 μm or 116 μm thrombin activity was higher with a slow approximately linear increase reaching 15000 au at 60 min.

In contrast thrombin activity on resins with a mean particle size of 198 μm exhibit a fast exponential increase, showing a more than 4 fold increase within the first 10 min up to approximately 18000 au and a continuing linear increase over the duration of observation reaching at 60 min more than 25 000 au.

The fast exponential increase of fluorescent signal upon addition of the substrate to resins containing thrombin may serves as a reliable indicator for preservation of thrombin activity after immobilization.

Standards indicate that free thrombin results in a fast increase in fluorescence signal as large amounts of the substrate are converted to its fluorescent product. Inhibition of the free movement of thrombin by covalent immobilization onto epoxy-terminated resins resulted in a linear increase in signal over time and/or resins with suboptimal particles sizes. While immobilization by electrostatic interactions to the amino groups of the amino-terminated resins, did not limit the free movement of thrombin and resulted in signal profiles similar to that of free thrombin, in particular when using particles with mean diameters of approximately 200 μm.

Results for the thrombin activity for different resin particle sizes are summarized in Table 3, indicating a substantial increase for preferred resin with particles sizes ranging from 150 to 300 μm.

Example 3: Dispenser Design

FIG. 5 depicts a schematic representation of a preferred embodiment of a dispenser 1, which takes the form of a single-barrel syringe. The dispenser 1 comprises a container 3 filled with a fibrinogen solution 8 situated upstream of an activation compartment 5. Within the activation compartment 5 a functionalized support 7 is located to which a coagulation factor, preferably thrombin is immobilized. A piston 11 equipped with a plug 13 allows for dispensing the sealant. By pushing the piston 11 the fibrinogen solution 8 is extruded from the container 3 and forced to pass the activation compartment 5. During this process fibrinogen-cleavage activity of the immobilized coagulation factor, preferably thrombin, generates polymerizing fibrin. A tip 9 allows for precise deposition of the resulting fibrin sealant at the desired site. Downstream of the activation compartment 5 the dispenser 1 preferably comprises a filter 15 to prevent the release of any part of the functionalized support 7 into the tip 9 and thus the site of deposition.

TABLE 1

Immobilization yield for thrombin
Table 1. Yield and final yield of thrombin immobilization on amino-terminated resins.

| Thrombin concentration (mg/mL) | Immobilization yield (mg) | Wash out (mg) | Final immobilization yield (mg/g) | μmol/g |
|---|---|---|---|---|
| 5 | 9.6 | 5.8 | 8.2 | 0.23 |
| 10 | 18.6 | 6.7 | 23.8 | 0.66 |
| 25 | 45.0 | 12.7 | 64.5 | 1.79 |
| 50 | 94.7 | 31.2 | 124.4 | 3.46 |

TABLE 2

Apparent activity of thrombin for different resin types

| Resin type | Immobilization concentration (mg/mL) | Thrombin grade | Fluorescence after 60 min (au) | Apparent activity (U/g resin) |
|---|---|---|---|---|
| Amino | 20 | 90-250 U/mg | 21397 | 6785 |
| Amino | 20 | >1500 U/mg | 28116 | 51226 |
| Epoxy | 20 | 90-250 U/mg | 10683 | 2920 |

TABLE 3

Comparison of thrombin activity for different sizes of resin particles

| Resin name | Size range (μm) | Mean size (μm) | Porosity (nm) | Acitivity* (%) |
|---|---|---|---|---|
| LifeTech ECR8409F | 150-300 | 198 | 60-120 | 100 |
| LifeTech ECR8415M | 300-710 | 413 | 120-180 | 57.5 |
| LifeTech ECR8409F | 150-300 | 198 | 60-120 | 100 |
| D6159 | 50-150 | 116 | 60-120 | 68.4 |
| D6161 | 30-80 | 59 | 120-180 | 64.2 |

*Max fluorescent signal of thrombin substrate as compared to ECR8409F in paired experiments

LIST OF REFERENCE SIGNS 1 dispenser
3 container
5 activation compartment
7 functionalized support
8 fibrinogen solution
9 tip
11 piston
13 plug
15 filter

The invention claimed is:

1. A dispenser of a sealant for hemostasis, comprising:
a container configured to receive a fibrinogen solution, and
an activation compartment,
the activation compartment being situated downstream of the container and comprising a functionalized support to which a coagulation factor is electrostatically immobilized, wherein the functionalized support is a functionalized resin comprising particles with a mean size of 150 to 300 µm.

2. The dispenser according to claim 1, wherein the coagulation factor is a fibrinogen-cleaving protease.

3. The dispenser according to claim 2, wherein the fibrinogen-cleaving protease is thrombin.

4. The dispenser according to claim 1, wherein the functionalized resin is an amino-functionalized resin.

5. The dispenser according to claim 4, wherein the amino-functionalized resin is an amino methacrylate resin.

6. The dispenser according to claim 1, wherein the functionalized resin comprises a spacer moiety to which a functionalized group is attached.

7. The dispenser according to claim 6, wherein the spacer moiety comprises or consists of an organic moiety comprising C2-C20.

8. The dispenser according to claim 7, wherein the organic moiety is a branched or unbranched alkyl, alkenyl, alkynyl, aryl, aminoalkyl, aminoalkenyl, aminoalkynyl, amide and/or aralkyl group, or combination thereof.

9. The dispenser according to claim 1, wherein at least 2000 units (U) of the coagulation factor are immobilized per gram (g) of the functionalized support.

10. The dispenser according to claim 9, wherein at least 5000 units (U) of the coagulation factor are immobilized per gram (g) of the functionalized support.

11. The dispenser according to claim 1, wherein the resin particles are porous particles with a mean pore diameter of 60 nm to 120 nm.

12. The dispenser according to claim 1, additionally comprising a piston equipped with a plug, said plug being configured to be received in the container and for extruding the fibrinogen solution from the container and through the activation compartment.

13. The dispenser according to claim 1 additionally comprising a filter situated downstream of the activation compartment, wherein said filter is configured to prevent release of the functionalized support.

14. The dispenser according to claim 1, wherein the dispenser comprises a main body comprising the container and an exchangeable tip, wherein the activation compartment is comprised in the exchangeable tip or the main body.

15. The dispenser according to claim 1, wherein the container is filled with a solution comprising fibrinogen.

16. A support for use in an activation compartment of the dispenser according to claim 1, producible by a method comprising:
providing the functionalized support,
providing a solution comprising the coagulation factor, and
incubating the solution comprising the coagulation factor with the functionalized support.

17. The support according to claim 16, wherein the coagulation factor is thrombin.

18. An exchangeable tip for use in the dispenser according to claim 1, wherein the exchangeable tip comprises means for a releasable attachment to a main body of the dispenser and the activation compartment.

19. The exchangeable tip according to claim 18, wherein the coagulation factor is thrombin.

20. A kit comprising
the dispenser according to claim 1,
the fibrinogen solution.

21. The kit of claim 20 further comprising instructions for a method for dispensing a sealant for the hemostasis.

22. A method for generating and dispensing a sealant to a desired site, comprising the steps of
providing a dispenser, the dispenser comprising
a container filled with a fibrinogen solution, and
an activation compartment,
wherein the activation compartment is situated downstream of the container and comprising a functionalized support to which a coagulation factor is electrostatically immobilized, and
dispensing the fibrinogen solution to the desired site, wherein upon dispensing, the fibrinogen solution passes through the activation compartment, thereby generating and dispensing polymerizing fibrin as a sealant.

23. The method according to claim 22, wherein the coagulation factor is thrombin.

* * * * *